United States Patent
Reddy et al.

(10) Patent No.: US 11,724,995 B2
(45) Date of Patent: Aug. 15, 2023

(54) DECALIN DERIVATIVES, A PROCESS FOR THE PREPARATION AND PHARMACEUTICAL COMPOSITION THEREOF

(71) Applicant: Council of Scientific & Industrial Research, New Delhi (IN)

(72) Inventors: Dumbala Srinivasa Reddy, Pune (IN); Kiran Ashok Kulkarni, Pune (IN); Hanuman Popat Kalmode, Pune (IN); Paresh Ramesh Athawale, Pune (IN); Suhag Sanjay Patil, Pune (IN); Raveena Vijay Rajput, Pune (IN); Yash Jignasu Mankad, Pune (IN); Namrata Nandkishor Patil, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 4 days.

(21) Appl. No.: 17/287,404

(22) PCT Filed: Oct. 22, 2019

(86) PCT No.: PCT/IN2019/050779
§ 371 (c)(1),
(2) Date: Apr. 21, 2021

(87) PCT Pub. No.: WO2020/084633
PCT Pub. Date: Apr. 30, 2020

(65) Prior Publication Data
US 2021/0395212 A1     Dec. 23, 2021

(30) Foreign Application Priority Data
Oct. 22, 2018 (IN) .............................. 201811039715

(51) Int. Cl.
*C07D 303/32* (2006.01)
*C07C 43/162* (2006.01)
*C07C 49/573* (2006.01)
*C07C 49/577* (2006.01)

(52) U.S. Cl.
CPC .......... *C07D 303/32* (2013.01); *C07C 43/162* (2013.01); *C07C 49/573* (2013.01); *C07C 49/577* (2013.01)

(58) Field of Classification Search
CPC ................................................. C07C 2602/28
See application file for complete search history.

(56) References Cited

U.S. PATENT DOCUMENTS 3,989,739 A    11/1976  Stadler et al.
5,571,939 A    11/1996  Christenson

FOREIGN PATENT DOCUMENTS

EP    0296564 A2    12/1988
EP    2067763 A2    6/2009

OTHER PUBLICATIONS

Kalmode, H., et al. "Total Synthesis and Biological Evaluation of Cell Adhesion Inhibitors Peribysin A and B: Structural Revision of Peribysin B." Org. Lett. (2018), vol. 20, pp. 7003-7006. (Year: 2018).*
Athawale, P., et al. "Overturning the Peribysin Family Natural Products Isolated from Periconia byssoides OUPS-N133: Synthesis and Stereochemical Revision of Peribysins A, B, C, F, and G." Org. Lett. (2020), vol. 22, pp. 3104-3109. (Year: 2020).*
Stonik, V., et al. "Chemical constituents of *Ligularia alticola* Worosch. leaves and their biological activities." Phytochemistry Letters. (2016), vol. 15, pp. 46-52. (Year: 2016).*
Yamada, T., et. al. "Absolute Stereostructures of Cell-adhesion Inhibitors, Peribysins A, E, F and G, Produced by a Sea Hare-derived *Periconia* sp." J. Antibiot. (2005), vol. 58, Issue 3, pp. 185-191. (Year: 2005).*
Yamada, Takeshi, et al. "Peribysins A-D, potent cell-adhesion inhibitors from a sea hare-derived culture of *Periconia* species." Org. Biomol. Chem. (2004), vol. 2, pp. 2131-2135. (Year: 2004).*
Corana, F., et al. "Terpenoids from Russula lepida and R. amarissima (Basidiomycota, Russulaceae." Phytochemistry. (2012), vol. 84, pp. 154-159. (Year: 2012).*
Kalmode, Hanuman P., et al. "Total Synthesis and Biological Evaluation of Cell Adhesion Inhibitors Peribysin A and B: Structural Revision of Peribysin B." Org. Lett. (2018), vol. 20, pp. 7003-7006. (Year: 2018).*
Haring et al., "Olfactory Studies on Enantiomeric Eremophilane Sesquiterpenoids", J. Agr. Food Chem., vol. 20, No. 5, 4 pgs., 1972.
Yamada et al., "Absolute sterostructures of cell-adhesion inhibitors, mascrophelides C, E-G and I, produced by *Periconia* species separated from *Aplysia* sea hare", J. Chem. Soc., Perkin Trans 1, pp. 3046-3053, 2001.

(Continued)

*Primary Examiner* — John S Kenyon
(74) *Attorney, Agent, or Firm* — Dinsmore & Shohl, LLP

(57) ABSTRACT

Decalin derivative compounds of formula (I) are provided, including processes for preparation thereof, and pharmaceutical compositions including the decalin derivative compounds. Methods are provided for treating blood related disorders, such as sickle cell anemia, in a subject in need thereof using a compound of formula (I).

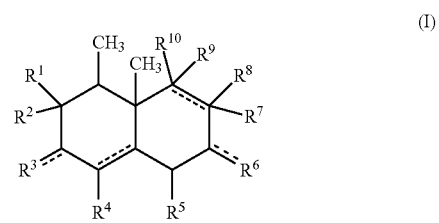

(I)

7 Claims, No Drawings

(56) References Cited

OTHER PUBLICATIONS

Yamada et al., "Absolute Sterostructures of Cell-adhesion Inhibitors, Perbysins A, E, F and G, Produced by a Sea Hare-derived *Periconia* sp.", The Journal of Antibiotics, vol. 58, No. 3, pp. 185-191, 2005.

Search Report pertaining to Application No. PCT/IN2019/050779 dated Jan. 24, 2020.

International Preliminary Report on Patentability pertaining to Application No. PCT/IN2019/050779 dated Apr. 27, 2021.

* cited by examiner

DECALIN DERIVATIVES, A PROCESS FOR THE PREPARATION AND PHARMACEUTICAL COMPOSITION THEREOF

CROSS REFERENCES TO RELATED APPLICATIONS

This application is a national-stage application under 35 U.S.C. § 371 of International Application No. PCT/IN2019/050779, filed Oct. 22, 2019, which international application claims benefit of priority to Indian Patent Application No. 201811039715, filed Oct. 22, 2018.

TECHNICAL FIELD

The present disclosure relates to decalin derivatives. More particularly, the present disclosure relates to decalin derivative compounds of formula (I), a process for preparation and a pharmaceutical composition thereof. The present disclosure further relates to a method for treating blood related disorders, preferably sickle cell anemia in a subject in need thereof using compound of formula (I).

BACKGROUND

Sickle cell anemia (SCA) is a genetic disorder in which the red blood cells assume a sickle shape instead of a normal disc shape. It occurs due to a mutation in which the amino acid glutamic acid is replaced by valine in the β-globin chain of hemoglobin. The sickle cell patient may suffer from pain, anemia, bacterial infections or stroke at different stages of his life. Treatment of SCA complications often includes antibiotics, pain management, intravenous fluids, blood transfusion and surgery. One of the complications of SCA is a painful condition called vaso-occlusion. The defective RBC's are more rigid and obstruct blood vessels resulting in restrict blood flow to the organs leading to multiple issues. The tendency of sickle RBC's to adhere to vascular endothelium is the root cause of vaso-occlusion. The adhesivity of theses defective RBC's is directly co-related with the severity of the disease. Some drugs targeting cell adhesion are under development for SCA are Rivipansel (Phase III); Propranolol, Sevuparin (Phase II). Along these lines, peribysins were isolated from a strain of *Periconia byssoides* OUPS-N133 originally separated from the sea hare, *Aplysia kurodai* by Yamada's group showed potent cell-adhesion inhibitory activity when they assayed using human leukemia HL60 cells to human umbilical vein endothelial cells (HUVECs). They are useful leads for the control of cancer metastasis and inflammation.

Attempts have been made to isolate or synthesize cell-adhesion inhibitors in the literature.

The article titled "Absolute stereo structures of cell-adhesion inhibitors, macrosphelides C, E-G and I, produced by a *Periconia* species separated from an *Aplysia* sea hare" by Takeshi Yamada et. al and published in the journal "*J. Chem. Soc., Perkin Trans. I*, 2001, 3046-3053" reports isolation of Macrosphelides E-I, along with known macrosphelides A and C, from a strain of *Periconia byssoides* originally separated from the sea hare *Aplysia kurodai*, and the elucidation of absolute stereo structures of macrosphelides E-G.

The article titled "Absolute Stereo structures of Cell-adhesion Inhibitors, Peribysins A, E, F and G, Produced by a Sea Hare-derived *Periconia* sp." by Takeshi Yamada et. al and published in the journal "J. Antibiot. 58(3): 185-191, 2005" reports isolation of Peribysins E~G (1~3) from a strain of *Periconia byssoides* originally separated from the sea hare *Aplysia kurodai* and elucidation of their absolute stereo structures.

Thus, isolation and elucidation of naturally occurring potent cell adhesion inhibitors Peribysin were reported in the literature.

Therefore, thus there is a need in the art for identifying and developing new cell adhesion inhibitors based on decalin (6,6-fused rings) (6,5-fused rings) scaffolds for treating sickle cell anemia and other blood related disorders.

SUMMARY

The main objective of this disclosure is to provide decalin derivative of formula (I), or a pharmaceutically acceptable salt thereof.

Another objective of this disclosure is to provide a process for the preparation of decalin derivative of formula (I).

Yet another objective of this disclosure is to provide a pharmaceutical composition comprising a compound of formula (I), or a stereoisomer, or ester or pharmaceutically acceptable salt thereof and a pharmaceutically acceptable carrier, diluent or excipient.

Still another objective of this disclosure is to provide a method for treating blood related disorders, preferably sickle cell anemia in a subject in need thereof; comprising administering to the subject a therapeutically effective amount of the compound of formula (I) or a pharmaceutically acceptable salt thereof.

In accordance with the above objectives, this disclosure provides decalin derivatives of formula (I), a process for preparation and pharmaceutical composition thereof.

In an aspect, the present disclosure provides decalin derivatives of formula (I) or a pharmaceutically acceptable salt thereof;

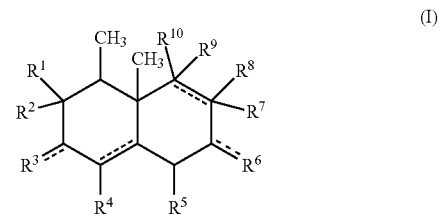

(I)

Wherein, $R^1$, $R^2$, $R^4$, $R^5$, $R^7$, $R^8$, $R^9$ and $R^{10}$ represents independently of each other hydrogen, or (un)substituted or substituted $C_1$-$C_{10}$ alkyl, $C_1$-$C_{10}$ alkenyl (un)substituted or substituted with hydroxy, alkoxy, ester, -OTBS; or amino, halo, hydroxyl, carbonyl, thiocarbonyl, carboxylic, alkoxy, carbamide, carbamate, hydrazine, or $R_1$ to $R_{10}$ may form a (un)substituted or substituted fused cyclic ring;

$R^3$ and $R^6$ represent hydrogen or oxygen;

$R^7$ or $R^8$ and $R^9$ or $R^{10}$ may form epoxide ring;

===== represents a single or double bond;

In another aspect, the present disclosure provides a process for the preparation of decalin derivatives of formula (I).

In yet another aspect, the present disclosure provides a pharmaceutical composition comprising a compound of formula (I), or a stereoisomer, or ester or pharmaceutically acceptable salt thereof and a pharmaceutically acceptable carrier, diluent or excipient.

In still another aspect, the present disclosure provides a method for treating blood related disorders, preferably sickle cell anemia in a subject in need thereof; comprising administering to the subject a therapeutically effective amount of the compound of formula (I) or a pharmaceutically acceptable salt thereof.

DETAILED DESCRIPTION

The invention will now be described in detail in connection with certain preferred and optional embodiments, so that various aspects thereof may be more fully understood and appreciated.

In the view of above, the present disclosure provides decalin derivative of formula (I) or a pharmaceutically acceptable salt thereof, a process for preparation thereof, and use of the compound of formula (I) or a pharmaceutically acceptable salt thereof for the treating blood related disorders, preferably sickle cell anemia.

In an embodiment, the present disclosure provides decalin derivative compound of formula (I) or a pharmaceutically acceptable salt thereof;

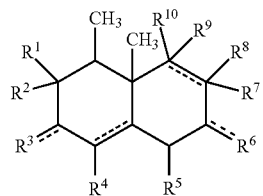

(I)

Wherein,
$R^1$, $R^2$, $R^4$, $R^5$, $R^7$, $R^8$, $R^9$ and $R^{10}$ represents independently of each other hydrogen, or (un)substituted or substituted $C_1$-$C_{10}$ alkyl, $C_1$-$C_{10}$ alkenyl (un)substituted or substituted with hydroxy, alkoxy, ester, -OTBS; or amino, halo, hydroxyl, carbonyl, thiocarbonyl, carboxylic, alkoxy, carbamide, carbamate, hydrazine, or $R_1$ to $R_{10}$ may form a (un)substituted or substituted fused cyclic ring;
$R^3$ and $R^6$ represent hydrogen or oxygen;
$R^7$ or $R^8$ and $R^9$ or $R^{10}$ may form epoxide ring;
===== represents a single or double bond;

In a preferred embodiment, the decalin derivatives of formula (I) is selected from the group consisting of 1-((4aR*,8R*,8aS*)-8,8a-Dimethyl-3,4,4a,7,8,8a-hexahydronaphthalen-2-yl)ethan-1-one (9), 1-((4aS*,8R*,8aS*)-8,8a-Dimethyl-3,4,4a,5,6,7,8,8a-octahydronaphthalen-2-yl)ethan-1-one (10), (1R*,4aS*,8aS*)-1,8a-Dimethyl-7-(prop-1-en-2-yl)-1,2,3,4,4a,5,6,8a-octahydronaphthalene (11), 2-((4aS*,8R*,8aS*)-8,8a-Dimethyl-3,4,4a,5,6,7,8,8a-octahydronaphthalen-2-yl)prop-2-en-1-ol (12), 2-((4aS*,8R*,8aS*)-8,8a-Dimethyl-3,4,4a,5,6,7,8,8a-octahydronaphthalen-2-yl)allyl acetate (12a), 2-((4aS,8R,8aS)-8,8a-Dimethyl-3-oxo-3,4,4a,5,6,7,8,8a-octahydronaphthalen-2-yl)allyl acetate (13), (1aR*,3aS*,7R*,7aS*,7bR*)-1a-(3-Hydroxyprop-1-en-2-yl)-7,7a-dimethyloctahydronaphtho[1,2-b]oxiren-2(1aH)-one (14), (1aS*,2R*,3aS*,7R*,7aS*,7bR*)-1a-(3-Hydroxyprop-1-en-2-yl)-7,7a-dimethyldecahydronaphtho[1,2-b]oxiren-2-ol (1) and (1aS*,2S*,3aS*,7R*,7aS*,7bR*)-1a-(3-hydroxyprop-1-en-2-yl)-7,7a-dimethyldecahydronaphtho[1,2-b]oxiren-2-ol (15), peribysin A, (4aS*,5R*,8aS*)-3-iodo-4a,5-dimethyl-4a,5,6,7,8,8a-hexahydronaphthalen-2(1H)-one (17), (4aS*,5R*,8aS*)-3-(3-(((tert-butyldimethylsilyl)oxy)prop-1-en-2-yl)-4a,5-dimethyl-4a,5,6,7,8,8a-hexahydronaphthalen-2(1H)-one (18), (4aS*,5R*,8aS*)-3-(3-hydroxyprop-1-en-2-yl)-4a,5-dimethyl-4a,5,6,7,8,8a-hexahydronaphthalen-2(1H)-one (19), (4R,4aS)-4,4a-dimethyl-4,4a,5,6-tetrahydronaphthalen-2(3H)-one (21), tert-butyl(((4R,4aS)-4,4a-dimethyl-2,3,4,4a,5,6-hexahydronaphthalen-2-yl)oxy)dimethylsilane, (4aS,5R)-4a,5-dimethyl-4,4a,5,6-tetrahydronaphthalen-2(3H)-one (24), (4R,4aS)-7,8-dihydroxy-4,4a-dimethyl-4,4a,5,6,7,8-hexahydronaphthalen-2(3H)-one (27), (4R,4aS)-6,7-dihydroxy-4,4a-dimethyl-4,4a,5,6,7,8-hexahydronaphthalen-2(3H)-one (28), (8R,8aS)-8,8a-dimethyl-1,7,8,8a-tetrahydronaphthalene-2,6-dione (29) and (1S,8aS)-1,8a-dimethyl-1,7,8,8a-tetrahydronaphthalene-2,6-dione (30).

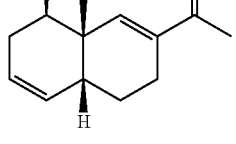

9

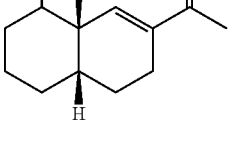

10

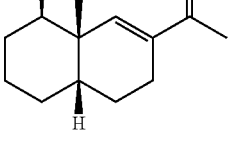

11

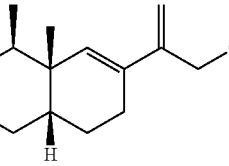

12

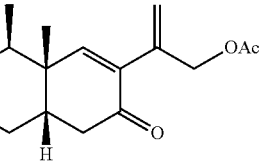

13

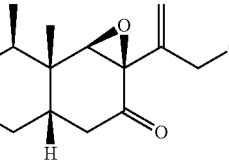

14

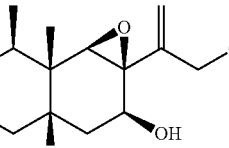

15

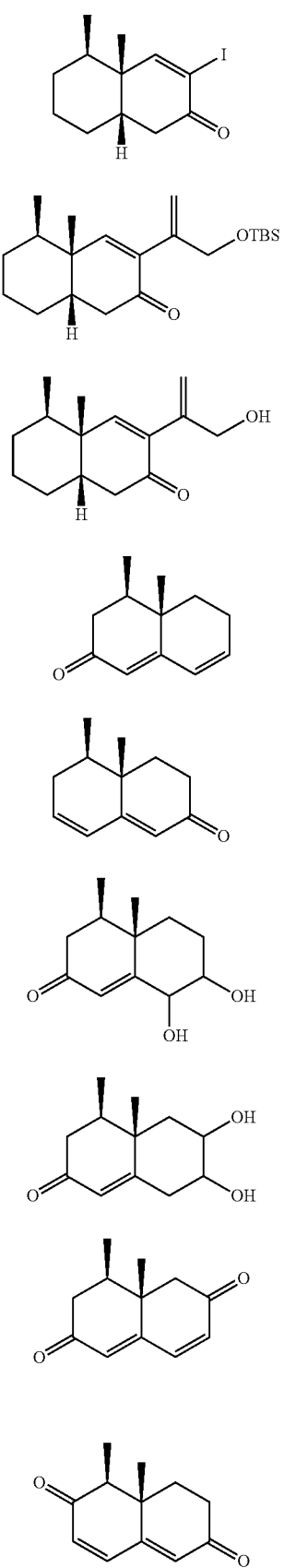

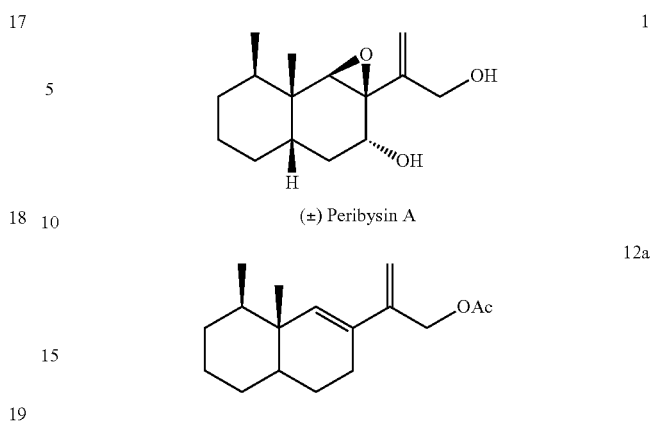

In another embodiment, the present disclosure provides a process for the preparation of decalin derivatives of formula (I) comprising:

(a) Reacting Lewis acid, base with compound of A1 and aldehyde to afford compound A2;
(b) Hydrogenating A2 to afford A3;
(c) Undergoing A3 in Witting reaction to afford A4;
(d) Carrying allylic oxidation on A4 to afford A5;
(e) Protecting and following allylic oxidation of A5 to afford A6;
(f) Epoxidating and deprotecting A6 to afford A7 and
(g) Reducing A7 to afford A8 and its analogues.

The process for the preparation of decalin derivatives of formula (I) is as depicted in scheme 1 below:

Scheme 1 General synthetic scheme

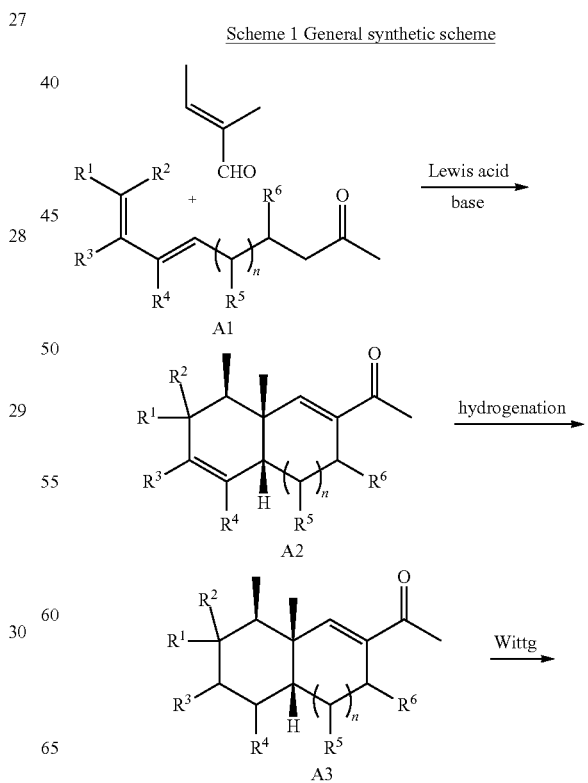

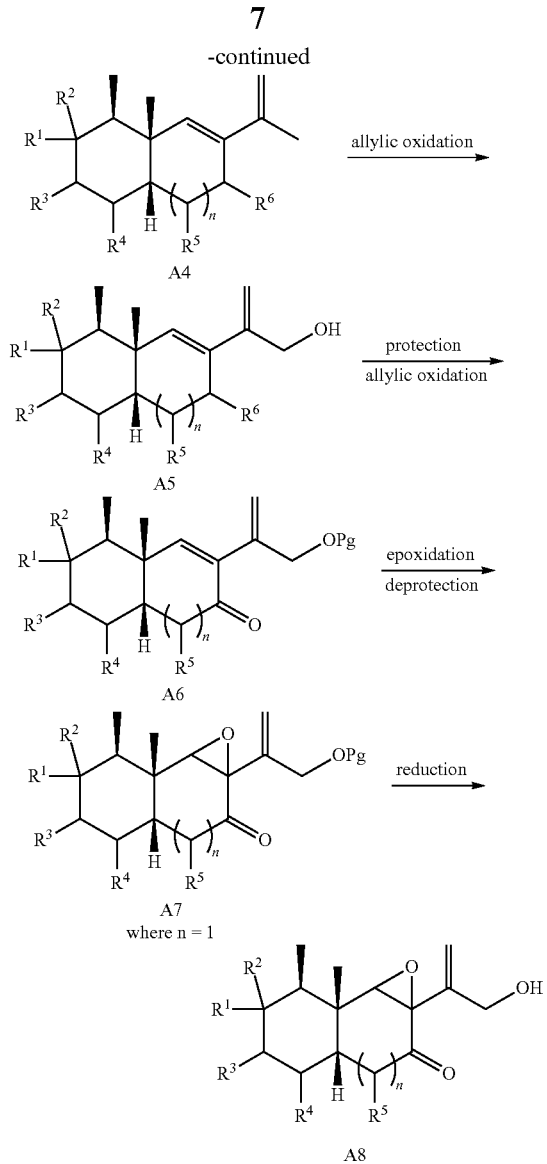

In a preferred embodiment, the present disclosure provides a process for the preparation of decalin derivatives of formula (I) comprising:
(a) Adding $BF_3.OEt_2$ dropwise at −78° C. to −80° C. to the reaction mixture of diene (A1) and (E)-2-methylbut-2-enal or (Z)-2-methylbut-2-enal in dry solvent to afford resultant mixture; stirring the resultant mixture at temperature in the range of 30 to 35° C. for the time period in the range of 12 to 14 hours to afford compound A2;
(b) Hydrogenating A2 with the help of a catalyst selected from $(PPh_3)_3RhCl$, Pd/C with $H_2$ or Pd/C with ammonium formate in dry solvent at temperature range of 30° C. to 35° C. for time period in the range of 12 to 14 hours to afford compound A3;
(c) Adding base selected from potassium tert-butoxide, NaH or n-BuLi to methyl triphenylphosphonium bromide or chloride in dry THF at temperature range in the range of 0 to −5° C. to afford canary yellow color solution adding enone A3 in THF to this canary yellow color solution followed by stirring the resultant reaction mixture at temperature range for 0 to −5° C. for the time period 1 to 2 hours to afford compound A4;
(d) Adding TBHP and $SeO_2$ or TBHP and $MnO_2$ or $Pd(OH)_2$ and TBHP to a solution of diene A4 in suitable solvent followed by stirring at temperature 30° C. to 35° C. for the time period in the range of 6 to 7 hours to afford crude product; adding $CeCl_3.7H_2O$ into solution of crude product in alcohol to form resultant reaction mixture; cooling resultant reaction mixture at the temperature ranging from −78° C. to 80° C.; adding $NaBH_4$ or $LiBH_4$ to the cooled reaction mixture and followed by stirring at temperature ranging from −78° C. to 80° C. for the time period ranging from 30 to 45 minutes to afford compound A5;
(e) Adding acetylating agents selected from acetic anhydride, acetyl Chloride in the presence of a base selected from pyridine, tri ethyl amine, or DMAP into solution of A5 in a solvent followed by stirring at temperature in the range of 30 to 35° C. for the time period in the range of 1 to 2 hours to afford compound diene acetate; adding PDC and TBHP or $CrO_3$ and pyridine or TBHP and $(MnOAc)_3$ to a solution of diene acetate in solvent followed by stirring at temperature in the range of 30 to 35° C. for the time period in the range of 6 to 7 hours to afford dienone acetate compound A6;
(f) Adding hydrogen peroxide and sodium hydroxide to a solution of A6 in methanol followed by stirring the reaction mixture at temperature in the range of 30 to 35° C. for the time period in the range of 6 to 7 hours to afford compound A7 and
(g) Adding $NaBH_4$ in the solution of epoxy alcohol in solvent followed by stirring the reaction mixture at temperature in the range of 0° C. to −5° C. for the time period in the range of 1 to 2 hours to afford compound A8.

The solvent used in step (a) to (g) is selected from THF, $CH_2Cl_2$, $Et_2O$, $CH_3CN$, toluene, 1,2-DCE, DMSO, t-butanol or methanol In still another embodiment, the present disclosure provides a process for the preparation of decalin derivatives of formula (I) comprising:
(a) Halogenating A9 to afford A10;
(b) Carrying Suzuki Coupling on A10 to afford A11;
(c) Epoxidating A11 to afford A12 and
(d) Reducing A12 to afford A13.

The process for the preparation of decalin derivatives of formula (I) is as depicted in scheme 2 below:

Scheme 2 Alternate synthetic scheme

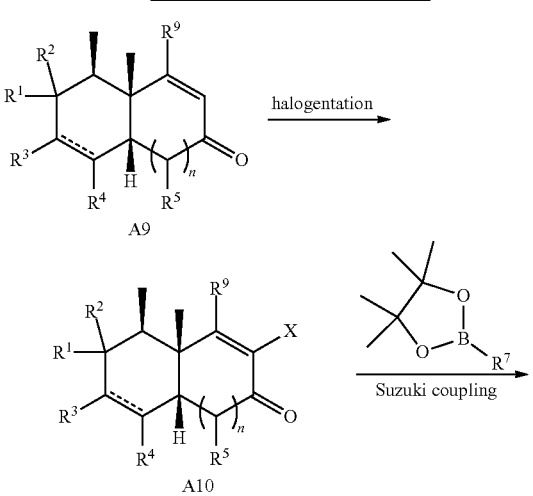

-continued

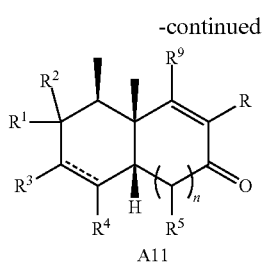
A11

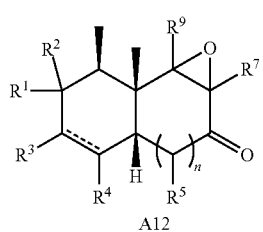
A12

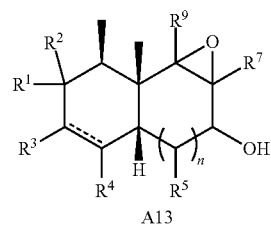
A13 where n = 1

In a preferred embodiment, the present disclosure provides a process for the preparation of decalin derivatives of formula (I) comprising:
(a) Adding iodine and base in enone A9 in suitable solvent followed by stirring the resultant reaction mixture at temperature in the range of 25° C. to 30° C. for the time period in the range of 24 to 30 hours to afford A10;
(b) Adding Pd(PhCN)$_2$C$_{1-2}$ to a mixture of vinyl iodide A10, alkenyl boronate, Ag$_2$O, triphenyl arsine in a solvent followed by stirring the reaction mixture at temperature 30° C. to 35° C. for the time period in the range of 4 to 5 hours to afford A11;
(c) Adding NaBH$_4$ or LiBH$_4$ to compound A12 in methanol at 0° C. and stirring for 30 min to afford A13.

The solvent used for steps (a) to (c) is selected from THF, CH$_2$Cl$_2$, Et$_2$O, CH$_3$CN, toluene, 1,2-DCE, DMSO, t-butanol or methanol In still yet another embodiment, the present disclosure provides a process for the preparation of decalin derivatives of formula (I) comprising:
(a) Undergoing Ozonolysis A14 to afford A15;
(b) Rearranging A15 to afford A16;
(c) Reducing and protecting A16 to afford A17;
(d) Epoxidating and reducing A17 to afford A18;
(e) Oxidating, deprotecting and rearranging A18 to afford A19;
(f) Hydrogenating A19 to afford A20 and
(g) Oxidating A20 to afford A21.

The process for the preparation of decalin derivatives of formula (I) is as depicted in scheme 3 below:

Scheme 3 Scheme for enantiopure compounds

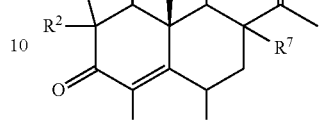
A14

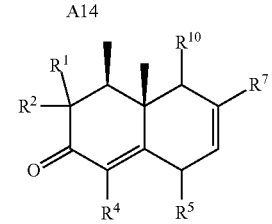
A15

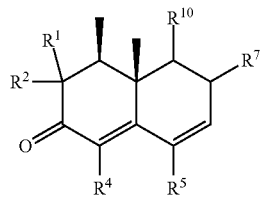
A16

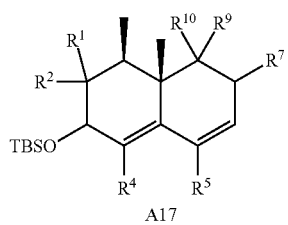
A17

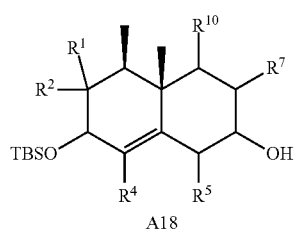
A18

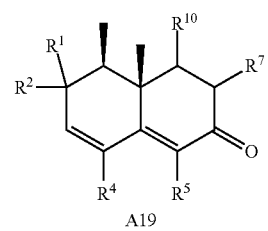
A19

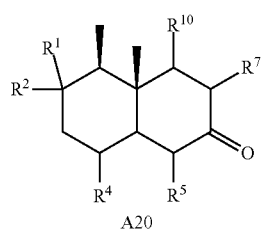
A20

-continued

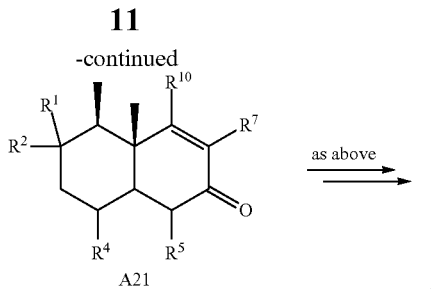
A21

In a preferred embodiment, the present disclosure provides a process for the preparation of decalin derivatives of formula (I) comprising:
(a) Bubbling ozone in the reaction mixture (+)-nootkatone in methanol at temperature ranging from −35° C. to −40° C., adding Cu(OAc)$_2$.H$_2$O or Cu(BF$_4$)$_2$ in water and FeSO$_4$.7H$_2$O or Fe(BF$_4$)$_2$ in water keeping the reaction mixture below −10° C. to −20° C. followed by stirring the reaction mixture at temperature in the range of 30° C. to 35° C. for time period in the range of 1 to 2 hours to afford crude product A15,
(b) Adding base selected from DBU, Et$_3$N, diisopropylethyl amine or N-methyl morpholine in solution of crude product A15 in solvent followed by stirring at temperature in the range of 30° C. to 35° C. for time period in the range of 4 to 5 hours to afford compound A16;
(c) Adding CeCl$_3$.7H$_2$O or without CeCl$_3$.7H$_2$O in dienone A16 in alcohol to afford reaction mixture, adding NaBH$_4$ in reaction mixture to afford allylic alcohol, dissolving allylic alcohol in solvent, adding imidazole followed by adding base selected from Et$_3$N or DMAP, and further adding TBSCl or TBSOTf followed by stirring for time period in the range of 12 to 14 hours to afford TBS diene A17;
(d) Adding m-CPBA or peracetic acid to a solution of TBS diene in solvent followed by stirring at temperature in the range of 0° C. to −5° C. for time period in the range of 30 min to 45 min to afford crude epoxide product, adding LAH LiBH$_4$, NaBH$_4$ or DIBAL-H in solution of crude epoxide product in solvent followed by stirring the reaction mixture at temperature in the range of 0° C. to −5° C. for time period in the range of 1 to 2 hours to afford crude alcohol compound A18;
(e) Adding NaHCO$_3$ and DMP, pyridinium dichromate (PDC) or pyridinium chloro chromate (PCC) to a solution of crude alcohol compound A18 in solvent followed by stirring at temperature in the range of 30° C. to 35° C. for time period in the range of 2 to 3 hours to afford crude TBS ketone, adding PTSA.H$_2$O or Camphorsulphonic acid to a solution of the ketone in a solvent followed by refluxing at temperature in the range of 40° C. to 45° C. for time period in the range of 1 to 2 hours to afford (−)-dienone compound A19;
(f) Adding 1% methanolic KOH solution to crude A19 followed by Pd/C and stirring under hydrogen atmosphere for 12 hours at 25 to 30° C. to provide A20. And
(g) adding IBX to A20 in DMSO and catalytic TFA at 60° C. and stirring for 2 hours to provide A21, and processing A 21; optionally Dihydroxylating A22 or A24 by OSO$_4$, NMO and t-BuOH, AD-mix alpha or AD-mix beta at temperature in the range of 0° C. to −5° C. for time period in the range of 2 to 3 hours to afford A23 or A25 respectively;

The solvent used for steps (a) to (h) is selected from THF, CH$_2$Cl$_2$, Et$_2$O, CH$_3$CN, toluene, 1,2-DCE, DMSO, t-butanol or methanol Preparation of A23, and A25 are as shown in scheme 4.

Scheme 4 Synthesis of enantiopure analogs

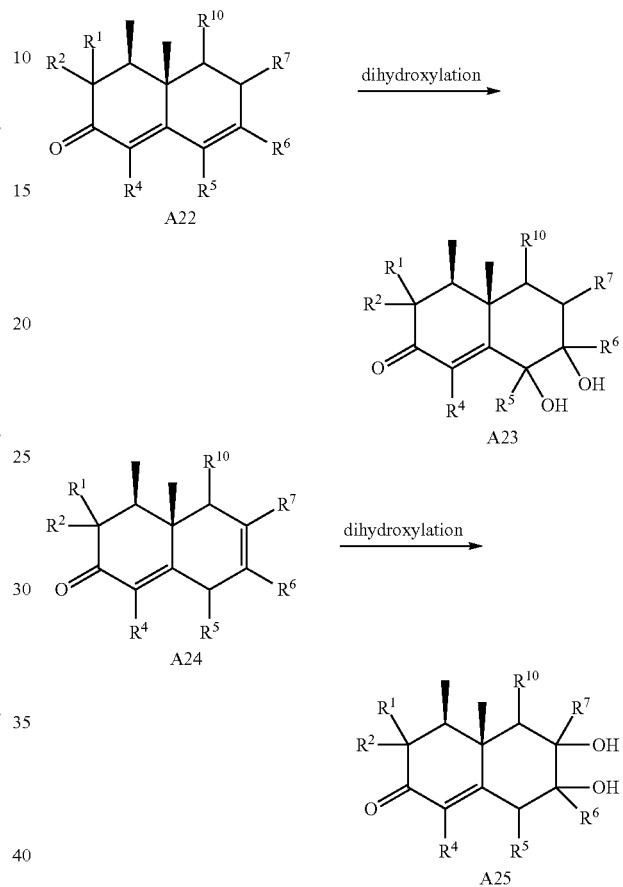

In yet another embodiment, the present disclosure provides a pharmaceutical composition comprising a compound of formula (I), or a stereoisomer, or ester or pharmaceutically acceptable salt thereof and a pharmaceutically acceptable carrier, diluent or excipient.

In still another embodiment, the present disclosure provides a method for treating blood related disorders, preferably sickle cell anemia in a subject in need thereof; comprising administering to the subject a therapeutically effective amount of the compound of formula (I) or a pharmaceutically acceptable salt thereof.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In another embodiment, the present disclosure relates to administering 'an effective amount' of the 'composition of disclosure' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the disclosure are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

In still yet another embodiment, the present disclosure provides Sickle cell adhesion inhibition using Sickle cell red blood cells (SS RBCs). Flow adhesion assay are performed with commercial microfluidic-well plate and microfluidic flow adhesion system. Microfluidic channels are coated by perfusion (1 dyne/cm$^2$, 5 min) and incubated (37° C., 1 h) with 100 ng/ml Fibronectin. Channels are then perfused with complete media to remove unbound Fibronectin. Then a uniform monolayer of HUVEC cells is formed by profusing micro channels with the cell suspension at a pressure of 3 dyne/cm$^2$ for 5 sec and kept for 12 hours incubation to form monolayer. The HUVEC monolayer is activated 25 ng/ml of TNF-α and incubated (37° C., 4 h). Meanwhile Sickle cell red blood cell (SS RBCs) are treated with test compound at 100 μM concentration and incubated in hypoxic condition (3% nitrogen, 5% $CO_2$, 2 h). Flow condition for adhesion assay was pulsatile (1.67 Hz) flow (0.3 dyne/cm$^2$). For adhesion inhibition assay SS RBCs are diluted (2:50) in PBS. SS RBCs are perfused over HUVEC monolayer and incubated for 1 h. Unbound cells in micro channels are removed by perfusing complete media. Adherent cells are enumerated. Table 1 depicts percentage of inhibition. Table 1 depicts percentage of inhibition when the compounds are tested at 100 μM concentration.

TABLE 1

| Compound | Structure | Inhibition |
|---|---|---|
| 21 | 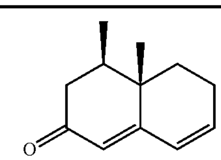 | 78% |
| 28 | 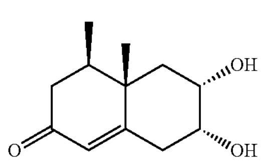 | 56% |

TABLE 1-continued

| Compound | Structure | Inhibition |
|---|---|---|
| 29 | 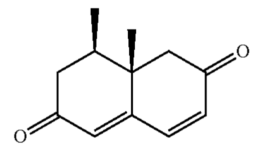 | 70% |
| 24 | 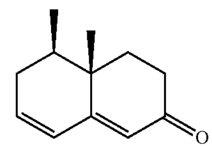 | 67% |
| 30 | 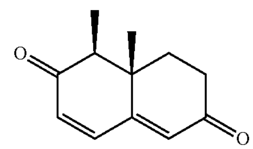 | 72% |

EXAMPLES

Following examples are given by way of illustration therefore should not be construed to limit the scope of the disclosure.

Example 1

Synthesis of 1-((4aR*,8R*,8aS*)-8,8a-Dimethyl-3,4,4a,7,8,8a-hexahydronaphthalen-2-yl)ethan-1-one (9)

To a solution of diene (7 g, 0.050 mol) and tiglic aldehyde (12.2 mL, 0.126 mol) in dry $CH_2Cl_2$ (300 mL) was added $BF_3 \cdot OEt_2$ (12.5 mL, 0.101 mol) dropwise at −78° C. The mixture was allowed to stir at 30° C. for a period of 12 h. After complete consumption of starting material checked by TLC, the $CH_2Cl_2$ layer was washed with saturated aqueous $NaHCO_3$ solution (3×50 mL) followed by $H_2O$ (50 mL) and brine (50 mL), dried over anhydrous $Na_2SO_4$, concentrated in vacuo. The crude material obtained after the removal of solvent was dissolved in methanol (50 mL), cooled to 0° C., followed by the dropwise addition of 15% aqueous KOH (30 mL) solution. After stirring for 6 h at room temperature, reaction mass was diluted with petroleum ether (300 mL), washed with water (50 mL), IN HCl (50 mL) and brine (50 mL), dried over anhydrous $Na_2SO_4$; concentrated in vacuo. Purification by flash column chromatography over silica gel (0.5:9.5; EtOAc-petroleum ether) afforded dienone (9, 4.76 g, 46%). Data for dienone (9): Light yellow oil; $IR_{vmax}$ (film): 1665, 1637, 1452, 1237 cm$^{-1}$; $^1$H NMR (500 MHz, $CDCl_3$) δ 6.64 (s, 1H), 5.60-5.56 (m, 1H), 5.53-5.48 (m, 1H), 2.28 (s, 3H), 2.12-2.00 (m, 2H), 1.93-1.88 (m, 2H), 1.90-1.63 (m, 3H), 1.43 (ddd, J=18.9, 9.15, 5.49 Hz, 1H), 1.00 (s, 3H), 0.96 (d, J=6.4 Hz, 3H); $^{13}$C NMR (125 MHz, $CDCl_3$) δ 198.0, 149.3, 137.8, 130.1, 125.5, 40.4, 37.3, 34.2, 31.6, 25.6, 25.5, 22.6, 21.1, 15.1; HRMS (ESI) calc for $C_{14}H_{21}O$ [M+H]$^+$ 205.1587, found 205.1586.

Example 2

Synthesis of 1-((4aS*,8R*,8aS*)-8,8a-Dimethyl-3,4,4a,5,6,7,8,8a-octahydronaphthalen-2-yl)ethan-1-one (10)

The dienone (9, 4.5 g, 0.022 mol) and Wilkinson's catalyst [(PPh$_3$)$_3$RhCl] (2 g, 2.205 mmol) were placed in an oven-dried round bottom flask. Dry benzene (100 mL) was added via syringe, the flask was then flushed with hydrogen gas to expel the argon. The reaction was allowed to proceed at 30° C. under hydrogen balloon pressure for 12 h. Upon completion of reaction (monitored by TLC), the mixture was passed through an alumina column and concentrated. Purification by flash chromatography over silica gel (0.5:9.5; EtOAc-petroleum ether) afforded enone (10, 3.9 g) in 86% yield.

Data for enone (10): Colorless liquid; IR$_{vmax}$ (film): 2926, 2864, 1667, 1634, 1456, 1379, 1266, 1234, 1029, 930, 757 cm$^{-1}$; $^1$H NMR (400 MHz, CDCl$_3$) δ 6.73 (s, 1H), 2.39 (dd, J=18.0, 3.5 Hz, 1H), 2.26 (s, 3H), 2.10-2.01 (m, 1H), 1.83-1.65 (m, 3H), 1.45 (dd, J=9.3, 4.1 Hz, 3H), 1.39-1.36 (m, 2H), 1.29-1.25 (m, 1H), 1.23-1.19 (m, 1H), 1.01 (s, 3H), 0.87 (d, J=6.8 Hz, 3H); $^{13}$C NMR (100 MHz, CDCl$_3$) δ 200.2, 151.0, 137.3, 39.5, 38.3, 36.5, 31.1, 28.0, 25.5, 23.9, 23.6, 21.2, 20.8, 16.0; HRMS (ESI) calc. for C$_{14}$H$_{23}$O [M+H]$^+$ 207.1743, found 207.1744.

Example 3

Synthesis of (1R*,4aS*,8aS*)-1,8a-Dimethyl-7-(prop-1-en-2-yl)-1,2,3,4,4a,5,6,8a-octahydronaphthalene (11)

To a suspension of methyl triphenylphosphonium bromide (17.8 g, 0.047 mol) in dry THF (60 mL) was added potassium tert-butoxide (5.3 g, 0.047 mol) at 0° C. After 5 minutes, the solution became canary yellow color, to that enone (10, 3.9 g, 0.018 mol) in THF (60 mL) was added and allowed to stirred at 0° C. for 1 h. The reaction was quenched with ice cold H$_2$O and extracted with diethyl ether (2×60 mL). Combined organic layer was washed with water (40 mL), brine (40 mL) and dried over anhydrous Na$_2$SO$_4$; concentrated in vacuo. Purification by flash chromatography over silica gel (1:9; EtOAc-petroleum ether) afforded diene (11, 3.3 g, 85%).

Data for diene (11): Colorless oil; IR$_{vmax}$ (film): 3020, 2927, 1654, 1625, 1215, 1038, 760, 667 cm$^{-1}$; $^1$H NMR (400 MHz, CDCl$_3$) δ 5.77 (s, 1H), 4.98 (s, 1H), 4.86 (s, 1H), 2.32 (dd, J=16.4, 4.3 Hz, 1H), 2.18 (dd, J=16.8, 9.8 Hz, 1H), 1.92 (s, 4H), 1.77-1.65 (m, 2H), 1.47-1.37 (m, 5H), 1.33-1.21 (m, 2H), 0.98 (s, 3H), 0.86 (d, J=6.8 Hz, 3H); $^{13}$C NMR (100 MHz, CDCl$_3$) δ 144.1, 136.3, 134.1, 110.2, 40.0, 37.4, 36.8, 31.2, 28.3, 26.1, 24.7, 21.6, 21.4, 21.0, 16.1; HRMS (ESI) calc. for C$_{15}$H$_{25}$ [M+H]$^+$ 205.1958, found 205.1960.

Example 4

Synthesis of 2-((4aS*,8R*,8aS*)-8,8a-Dimethyl-3,4,4a,5,6,7,8,8a-octahydronaphthalen-2-yl)prop-2-en-1-ol (12)

To a solution of diene (11, 3.3 g, 16.17 mmol) in CH$_2$Cl$_2$ (120 mL) at 0° C. was added TBHP (5.0-6.0 M in decane, 5.3 mL, 32.35 mmol) and SeO$_2$ (0.95 g, 8.085 mmol). Then the reaction was allowed to warm to 30° C. and stirred for 6 h, before it was quenched with saturated aqueous Na$_2$S$_2$O$_3$ (80 mL) solution at 0° C. The layers were separated and the aqueous layer was extracted with CH$_2$Cl$_2$ (4×40 mL). The combined organic layers were dried over Na$_2$SO$_4$, filtered and concentrated under reduced pressure to afford crude product as mixture.

To a solution of the above crude mixture in CH$_2$Cl$_2$ (60 mL) and MeOH (60 mL) at rt was added CeCl$_3$.7H$_2$O (12.1 g, 32.35 mmol). After it was cooled to -78° C., NaBH$_4$ (1.2 g, 32.35 mmol) was added slowly to the reaction mixture and it was stirred at -78° C. for 30 min. The reaction was quenched with saturated aqueous NH$_4$Cl (40 mL) solution at 0° C. and the mixture was concentrated under reduced pressure, filtered through a pad of Celite and washed with EtOAc. The layers were separated and the aqueous layer was extracted with EtOAc (4×60 mL). Then the combined organic layers were dried over Na$_2$SO$_4$, filtered and concentrated under reduced pressure. The residue was purified by flash column chromatography on silica gel (6:1; petroleum ether-EtOAc) to provide allyl alcohol (12, 2.4 g) in 67% yield over 2 steps.

Data for allyl alcohol (12): Colorless oil; IR$_{vmax}$ (film): 3416, 2927, 2866, 1669, 1454, 1376, 1220, 1041,761, 665 cm$^4$; $^1$H NMR (400 MHz, CDCl$_3$) δ 5.79 (s, 1H), 5.12 (d, J=4.9 Hz, 2H), 4.34 (s, 2H), 2.27 (dd, J=16.5, 4.6 Hz, 1H), 2.20-2.12 (m, 1H), 1.91 (ddd, J=18.4, 12.7, 5.9 Hz, 1H), 1.78-1.65 (m, 3H), 1.47-1.45 (m, 3H), 1.38 (d, J=13.7 Hz, 2H), 1.26-1.16 (m, 2H), 0.96 (s, 3H), 0.84 (d, J=6.8 Hz, 3H); $^{13}$C NMR (100 MHz, CDCl$_3$) δ 147.5, 136.1, 131.7, 110.1, 64.4, 39.9, 37.4, 36.8, 31.1, 28.2, 26.4, 24.4, 21.5, 21.3, 16.1; HRMS (ESI) calc. for C$_{15}$H$_{23}$O [M-H]$^-$ 219.1743, found 219.1743.

Example 5

Synthesis of 2-((4aS*,8R*,8aS*)-8,8a-Dimethyl-3,4,4a,5,6,7,8,8a-octahydronaphthalen-2-yl)allyl acetate: (12a)

To a solution of compound allyl alcohol 12 (2.0 g, 9.09 mmol) in CH$_2$Cl$_2$ (60 mL) at 0° C. was added DMAP (2.2 g, 18.18 mmol) and Ac$_2$O (3.4 mL, 36.3 mmol). Then the reaction was allowed to warm to 30° C. and stirred for 1 h, before it was quenched with saturated aqueous NaHCO$_3$ (20 mL) solution at 0° C. The layers were separated and the aqueous layer was extracted with CH$_2$Cl$_2$ (2×30 mL). The combined organic layers were dried over Na$_2$SO$_4$, filtered and concentrated under reduced pressure to afford diene acetate (1.90 g) in 80% yield.

Data for diene acetate: Yellowish oily liquid; IR$_{vmax}$ (film): 3022, 2928, 2865, 1732, 1605, 1452, 1375, 1220, 1033, 761 cm$^{-1}$; $^1$H NMR (400 MHz, CDCl$_3$) δ 5.71 (s, 1H), 5.17 (s, 1H), 5.11 (s, 1H), 4.77 (dt, J=18.5, 12.9 Hz, 2H), 2.29-2.23 (m, 1H), 2.15 (ddd, J=12.1, 9.6, 6.4 Hz, 1H), 2.07 (s, 3H), 1.93-1.88 (m, 1H), 1.76-1.63 (m, 2H), 1.48-1.43 (m, 3H), 1.36 (dd, J=10.1, 6.8 Hz, 2H), 1.27-1.18 (m, 2H), 0.94 (s, 3H), 0.82 (d, J=6.8 Hz, 3H); $^{13}$C NMR (100 MHz, CDCl$_3$) δ 170.9, 142.7, 136.8, 131.3, 112.6, 65.6, 39.9, 37.5, 36.7, 31.1, 28.2, 26.2, 24.4, 21.5, 21.3, 21.1, 16.0; HRMS (ESI) calc. for C$_{17}$H$_{27}$O$_2$ [M+H]$^+$ 263.2013, found 263.2015.

Example 6

Synthesis of 2-((4aS,8R,8aS)-8,8a-Dimethyl-3-oxo-3,4,4a,5,6,7,8,8a-octahydronaphthalen-2-yl)allyl acetate (13)

To a solution of the diene acetate (1.0 g, 3.81 mmol) in benzene 60 mL at 0° C. were added PDC (7.12 g, 19.08 mmol) and TBHP (5.0-6.0 M in decane, 2.45 mL, 19.08 mmol). After the reaction mixture was stirred for 15 min, it was brought to 30 deg C. and further stirred for 6 h. The reaction mixture was diluted with ethyl acetate (40 mL), filtered through a pad of celite, and washed with ethyl acetate (2×10 mL). The obtained filtrate was concentrated in vacuo and purified by flash column chromatography over silica gel (2:8; EtOAc-petroleum ether) afforded dienone acetate (13, 0.245 g, 43% brsm) and recovered diene acetate (0.455 g).

Data for dienone acetate (13): Colorless oil; $IR_{vmax}$ (film): 3026, 2930, 2868, 1735, 1668, 1607, 1456, 1377, 1222, 1035, 957, 768 $cm^{-1}$; $^1H$ NMR (400 MHz, $CDCl_3$) δ 6.69 (s, 1H), 5.23 (s, 1H), 5.18 (s, 1H), 4.74 (q, J=13.1 Hz, 2H), 2.67 (dd, J=17.0, 12.3 Hz, 1H), 2.26 (dd, J=17.0, 4.3 Hz, 1H), 2.08-2.02 (m, 1H), 1.99 (s, 3H), 1.80 (ddd, J=13.6, 6.8, 3.4 Hz, 1H), 1.76-1.67 (m, 1H), 1.56-1.51 (m, 1H), 1.48-1.42 (m, 2H), 1.36-1.31 (m, 2H), 1.11 (s, 3H), 0.91 (d, J=6.8 Hz, 3H); $^{13}C$ NMR (100 MHz, $CDCl_3$) δ 198.8, 170.5, 158.8, 141.6, 136.3, 117.0, 66.1, 40.0, 39.6, 39.1, 35.9, 30.2, 27.0, 20.9, 20.7, 20.4, 15.9; HRMS (ESI) calc. for $C_{17}H_{25}O_3$ $[M+H]^+$ 277.1805, found 277.1804.

Example 7

Synthesis of (1 aR*,3aS*,7R*,7aS*,7bR*)-1a-(3-Hydroxyprop-1-en-2-yl)-7,7a-dimethyloctahydronaphtho[1,2-6]oxiren-2(1aH)-one (14)

To a mixture of dienone acetate (13, 0.110 g, 0.398 mmol) in MeOH (15 mL) was added hydrogen peroxide (30% aqueous solution, 0.30 mL, 3.188 mmol), 10% aq. sodium hydroxide (0.25 mL) solution dropwise at 0° C. The reaction mixture was allowed to warm gradually to 30° C. After 4 h, more 10% aq. sodium hydroxide (0.750 mL) was added and stirred for additional 2 h. The reaction mixture was filtered, followed by addition of 5 mL saturated aqueous $NaHCO_3$ solution and extracted with EtOAc (3×10 mL). The organic extracts were washed with brine (5 mL), dried over $Na_2SO_4$, and concentrated to afford crude product. Which was purified by flash column chromatography over silica gel (2:8; ethyl acetate-petroleum ether) to obtained epoxy alcohol (14) as inseparable mixture as a yellowish solid (0.083 g, 83%).

Data for epoxy alcohol (14): Yellowish solid; mp 86-88° C. (decomp.); $IR_{vmax}$ (film): 3411, 2926, 2864, 1702, 1453, 1378, 1024, 912, 762 $cm^{-1}$; $^1H$ NMR (400 MHz, $CDCl_3$) δ 5.33 (s, 1H), 5.26 (s, 1H), 5.10 (s, 1H), 5.04 (s, 1H), 4.70 (d, J=13.3 Hz, 1H), 4.50 (d, J=13.3 Hz, 1H), 4.28 (d, J=12.8 Hz, 1H), 4.18 (d, J=13.0 Hz, 1H), 3.36 (s, 1H), 3.28 (s, 1H), 2.93 (s, 1H), 2.45 (dd, J=18.8, 11.3 Hz, 1H), 2.31 (dd, J=18.6, 6.7 Hz, 1H), 2.12 (s, 1H), 2.06 (t, J=13.7 Hz, 1H), 1.74-1.61 (m, 4H), 1.55 (d, J=14.2 Hz, 1H), 1.49-1.34 (m, 6H), 1.29-1.25 (m, 3H), 1.20 (s, 2H), 1.11 (s, 3H), 0.95 (d, J=6.7 Hz, 2H), 0.91 (d, J=6.6 Hz, 3H); $^{13}C$ NMR (100 MHz, $CDCl_3$) δ 207.0, 143.3, 143.2, 115.8, 106.5, 99.5, 72.3, 71.4, 68.2, 66.7, 64.2, 64.1, 38.7, 37.2, 37.1, 36.3, 33.4, 32.9, 32.2, 30.9, 30.6, 29.9, 26.6, 25.6, 20.5, 19.9, 17.4, 16.7, 16.4, 16.3; HRMS (ESI) calc. for $C_{15}H_{22}O_3Na$ [M+Na]+273.1461, found 273.1458.

Example 8

Synthesis of (1aS*,2R*,3aS*,7R*,7aS*,7bR*)-1a-(3-Hydroxyprop-1-en-2-yl)-7,7a-dimethyldecahydronaphtho[1,2-6]oxiren-2-ol (1) and (1aS*,2S*,3aS*,7R*,7aS*,7bR*)-1a-(3-hydroxyprop-1-en-2-yl)-7,7a-dimethyldecahydronaphtho[1,2-6]oxiren-2-ol (15)

To an inseparable mixture of epoxy alcohol (14, 0.050 g, 0.200 mmol) in MeOH (4 mL) was added $NaBH_4$ (0.019 g, 0.500 mmol) in small portions at 0° C. The reaction mixture was stirred for 1 h at same temperature, quenched with saturated $NH_4Cl$ (5 mL) solution and extracted with ethyl acetate (3×10 mL). The combined organic layers were washed with brine (5 mL), dried over $Na_2SO_4$, filtered and concentrated. The obtained crude product was purified by flash column chromatography (10:90; ethyl acetate-petroleum ether) to afford peribysin A (1, 0.039 g) and its diastereomer (15, 0.005 g) in 88% of total yield.

Data for peribysin A (1): Colorless crystalline solid; mp 98-100° C.; $IR_{vmax}$ (film): 3357, 2929, 2868, 1647, 1453, 1051,925,765 $cm^{-1}$; $^1H$ NMR (500 MHz, $CDCl_3$) δ 5.31 (s, 1H), 5.20 (s, 1H), 4.32 (d, J=11.7 Hz, 1H), 4.15 (d, J=11.7 Hz, 1H), 4.01 (d, J=6.5 Hz, 1H), 3.34 (br s, 2H), 3.17 (s, 1H), 1.95 (s, 1H), 1.81 (d, J=11.4 Hz, 1H), 1.68 (m, 1H), 1.52-1.44 (m, 4H), 1.33 (br d, J=13.3 Hz, 1H), 1.25 (m, 2H), 1.05 (s, 3H), 0.94 (d, J=6.1 Hz, 3H); $^{13}C$ NMR (125 MHz, $CDCl_3$) δ 145.6, 117.3, 69.8, 68.5, 67.2, 64.2, 35.7, 33.1, 32.5, 31.0, 30.7, 26.9, 20.4, 16.6 (2C); HRMS (ESI) calc. for $C_{15}H_{24}O_3Na$ $[M+Na]^+$ 275.1618, found 275.1616.

Data for its diastereomer (15): Colorless crystalline solid; low melting solid; $IR_{vmax}$ (film): 3382, 2927, 2864, 1647, 1454, 1388, 1071, 1036, 941, 756 $cm^{-1}$; $^1H$ NMR (400 MHz, $CDCl_3$) δ 5.21 (s, 1H), 5.15 (s, 1H), 4.31 (dd, J=13.2, 12.0 Hz, 1H), 4.22 (d, J=2.9 Hz, 1H), 4.16 (d, J=13.3 Hz, 1H), 3.23 (s, 1H), 2.67 (s, 1H), 2.00 (td, J=14.0, 5.3 Hz, 1H), 1.75-1.60 (m, 4H), 1.43 (d, J=10.2 Hz, 3H), 1.29 (d, J=14.2 Hz, 3H), 1.09 (s, 3H), 0.92 (d, J=6.8 Hz, 3H); $^{13}C$ NMR (100 MHz, $CDCl_3$) δ 147.5, 114.0, 71.2, 66.6, 65.4, 64.0, 35.8, 32.5, 31.4, 30.8, 30.0, 26.6, 20.5, 17.4, 16.5; HRMS (ESI) calc. for $C_{15}H_{24}O_3Na$ $[M+Na]^+$ 275.1618, found 275.1617.

Example 9

Synthesis of (4aS*,5R*,8aS*)-3-iodo-4a,5-dimethyl-4a,5,6,7,8,8a-hexahydronaphthalen-2(1H)-one (17)

To a cold solution of enone (16, 0.250 g, 1.40 mmol) in dry dichloromethane (5 mL) at 0° C. was added $I_2$ (0.712 g, 2.80 mmol) in dichloromethane (5 mL) and pyridine (2.15 mL, 26.64 mmol). The resultant mixture was gradually warmed to 30° C. and stirred for 24 h, quenched with saturated $Na_2S_2O_3$ (40 mL) solution and extracted with ethyl acetate (3×30 mL). The obtained organic layer was washed with $H_2O$ (25 mL), followed by brine (30 mL) and dried over anhydrous sodium sulfate, filtered and concentrated. The obtained crude product was purified by column chromatography (05:95; ethyl acetate-petroleum ether) to afford vinyl iodide (17, 0.362 g, 85%), as a light yellow oil, which solidified upon standing.

Data for vinyl iodide (17): Yellowish solid; mp 80-82° C.; $IR_{vmax}$ (film): 2927, 1681, 1584, 1461, 1322, 1159, 1004, 937, 898, 712 $cm^{-1}$; $^1H$ NMR (400 MHz, $CDCl_3$) δ 7.61 (s, 1H), 2.82 (dd, J=16.9, 12.6 Hz, 1H), 2.49 (dd, J=17.0, 4.2 Hz, 1H), 2.12 (ddd, J=12.3, 8.3, 4.0 Hz, 1H), 1.84 (ddd, J=17.0, 8.5, 5.0 Hz, 1H), 1.77-1.68 (m, 1H), 1.56-1.52 (m, 1H), 1.48 (dd, J=12.4, 3.6 Hz, 1H), 1.36 (d, J=3.7 Hz, 1H), 1.33-1.31 (m, 1H), 1.26 (dd, J=15.2, 3.6 Hz, 1H), 1.13 (s, 3H), 0.93 (d, J=6.9 Hz, 3H); $^{13}$C NMR (100 MHz, CDCl$_3$) δ 193.1, 169.6, 102.2, 44.2, 40.0, 38.5, 35.7, 30.2, 27.0, 20.4, 20.2, 16.1. HRMS (ESI) calc. for $C_{12}H_{18}OI$ [M+H]$^+$ 305.0397, found 305.0393.

Example 10

Synthesis of (4aS*,5R*,8aS*)-3-(3-((tert-butyldimethylsilyl)oxy)prop-1-en-2-yl)-4a,5-dimethyl-4a,5,6,7,8,8a-hexahydronaphthalen-2(1H)-one (18)

To a mixture of vinyl iodide (17, 1.2 g, 3.94 mmol), alkenyl boronate (1.765 g, 5.92 mmol), Ag$_2$O (1.472 g, 6.35 mmol), triphenyl arsine (0.136 g, 0.45 mmol) in THF (37.5 mL) and H$_2$O (4.7 mL) was added Pd(PhCN)$_2$C$_{1-2}$ (0.152 g, 0.394 mmol) at 30° C. and stirred for 4 h under nitrogen in the dark. The reaction mixture was quenched with saturated aqueous ammonium chloride (30 mL) solution and stirred for 30 minutes. The reaction mixture was filtered through a pad of celite followed by extraction with ethyl acetate (3×50 mL). The organic extracts were washed with brine (70 mL), dried over Na$_2$SO$_4$, and concentrated to afford crude product. Which was purified by column chromatography (04:96; ethyl acetate-petroleum ether) to obtained TBS dienone (18, 1.21 g, 88%), as a light yellow oil.

Data for TBS dienone (18): Light yellow oil; IR$_{vmax}$ (film): 2928, 1677, 1462, 1360, 1251, 1082, 902, 833, 774 cm$^{-1}$; $^1$H NMR (400 MHz, CDCl$_3$) δ 6.73 (s, 1H), 5.23 (s, 1H), 5.06 (s, 1H), 4.33-4.25 (m, 2H), 2.69 (dd, J=16.8, 12.7 Hz, 1H), 2.24 (dd, J=17.0, 4.2 Hz, 1H), 2.09-2.03 (m, 1H), 1.82 (ddd, J=10.1, 6.7, 3.3 Hz, 1H), 1.73-1.69 (m, 1H), 1.57-1.52 (m, 1H), 1.49-1.45 (m, 2H), 1.38-1.34 (m, 1H), 1.30 (dd, J=14.0, 2.9 Hz, 1H), 1.12 (s, 3H), 0.92 (d, J=6.8 Hz, 3H), 0.88 (s, 9H), 0.04 (s, 6H); $^{13}$C NMR (100 MHz, CDCl$_3$) δ 199.3, 158.6, 146.5, 137.2, 113.8, 65.2, 40.1, 39.8, 39.1, 35.8, 30.3, 27.1, 26.0 (3C), 20.7, 20.6, 18.4, 16.1, −5.22 (2C); HRMS (ESI) calc. for $C_{21}H_{36}O_2NaSi$ [M+Na]$^+$ 371.2377, found 371.2372.

Example 11

Synthesis of (4aS*,5R*,8aS*)-3-(3-hydroxyprop-1-en-2-yl)-4a,5-dimethyl-4a,5,6,7,8,8a-hexahydronaphthalen-2(1H)-one (19)

To a solution of TBS dienone (18, 1.0 g, 2.90 mmol) in anhydrous THF (45 mL) was added TBAF (2.87 mL, 1M in THF, 2.90 mmol) dropwise at 0° C. under nitrogen atmosphere. The resultant mixture was stirred at same temperature for 1 h and quenched with saturated aqueous ammonium chloride (30 mL) solution and extracted with ethyl acetate (3×70 mL). The organic extracts were washed with brine (70 mL), dried over Na$_2$SO$_4$, and concentrated to afford crude product. The obtained crude product was purified by column chromatography (20:80; ethyl acetate-petroleum ether) to obtained dienone alcohol (19, 0.550 g, 82%), as a yellowish oily liquid.

Data for dienone alcohol (19): Yellowish oily liquid; IR$_{vmax}$ (film): 3419, 2925, 1668, 1459, 1356, 1229, 1038, 985, 904, 723 cm$^{-1}$; $^1$H NMR (400 MHz, CDCl$_3$) δ 6.79 (s, 1H), 5.23 (s, 1H), 5.13 (s, 1H), 4.14 (s, 2H), 3.18 (s, 1H), 2.73 (dd, J=17.0, 12.8 Hz, 1H), 2.28 (dd, J=17.2, 4.0 Hz, 1H), 2.09-2.05 (m, 1H), 1.84-1.80 (m, 1H), 1.78-1.69 (m, 1H), 1.55 (ddd, J=11.7, 8.1, 3.8 Hz, 1H), 1.48 (d, J=1.7 Hz, 1H), 1.45 (s, 1H), 1.38-1.29 (m, 2H), 1.13 (s, 3H), 0.92 (d, J=6.8 Hz, 3H); $^{13}$C NMR (100 MHz, CDCl$_3$) δ 200.9, 159.8, 146.7, 138.0, 116.9, 65.3, 40.0, 39.7, 39.2, 35.8, 30.2, 27.0, 20.6, 20.5, 16.0; HRMS (ESI) calc. for $C_{15}H_{23}O_2$ [M+H]$^+$ 235.1693, found 235.1690.

Example 12

Synthesis of (4R,4aS)-4,4a-dimethyl-4,4a,5,6-tetrahydronaphthalen-2(3H)-one (21)

A stirred solution of (+)-nootkatone (10.0 g, 45.87 mmol) in methanol (70 mL) was cooled to −40° C. using dry ice-acetone bath. Ozone was bubbled through the solution keeping the temperature below −35° C. until the starting material was completely consumed monitored by TLC (approx. 40 min). Then the excess ozone was ceased by bubbling oxygen for two minutes followed by purging the nitrogen for 4 min. Then 30% W/Y solution of Cu(OAc)$_2$.H$_2$O (10.9 g, 55.05 mmol) in water FeSO$_4$.7H$_2$O (19.2 g, 68.80 mmol) in water were added sequentially over 4 min keeping the reaction temperature below −10° C. The reaction mixture was allowed to warm to 30° C. gradually and stirred for 1 h. After 1 h reaction mixture was filtered through celite and diluted with ethyl acetate (150 mL), washed with water (50 mL), IN HCl (50 mL) and brine (40 mL). The crude reaction mixture was dried over anhydrous sodium sulfate concentrated to give pale yellow oil (7.6 g crude) which was used as such for further reaction. To above crude compound (7.6 g, 43.18 mmol) in acetonitrile (80 mL) at 0° C. was added DBU (7.1 mL, 47.5 mmol) and stirred at 30° C. for 4 h. Then the acetonitrile was evaporated under reduced pressure and reaction mixture was diluted with EtOAc (100 mL), washed with water (50 mL), IN HCl (60 mL) and brine (40 mL). The organic layer was dried over sodium sulfate, evaporated and purified by column chromatography (silica gel) (4% EtOAc:pet ether) to give dienone (21), 4.32 g (53% over two steps) as a pale yellow oil and compound. Data for dienone (21): Pale yellow oil; $[α]_D^{23}$=+203.0 (c=1.0, CHCl$_3$); IR$_{vmax}$ (film): 1653, 1618, 1286 cm$^{-1}$; $^1$H NMR (400 MHz, CDCl$_3$) δ 6.18-6.16 (m, 1H), 6.08 (d, J=9.5 Hz, 1H), 5.62 (s, 1H), 2.34-2.21 (m, 4H), 2.01-1.91 (m, 1H), 1.86-1.82 (m, 1H), 1.33-1.25 (m, 1H), 0.95 (s, 3H), 0.91 (d, J=6.8 Hz, 3H); $^{13}$C NMR (100 MHz, CDCl$_3$) δ 200.0, 163.4, 137.9, 128.0, 124.0, 42.5, 39.1, 36.4, 32.6, 23.5, 15.5, 14.9; HRMS (ESI) calc. for $C_{12}H_{17}O$ [M+H]$^+$ 177.1274, found 177.1273.

Example 13

Synthesis of tert-butyl(((4R,4aS)-4,4a-dimethyl-2,3,4,4a,5,6-hexahydronaphthalen-2-yl)oxy) dimethylsilane (22)

A solution of dienone (21, 3.5 g, 19.88 mmol) in MeOH (40 mL) was cooled to 0° C. and added CeCl$_3$.7H$_2$O (11.1 g, 29.83 mmol). After stirring the reaction mixture for 10 min, NaBH$_4$ (1.5 g, 39.772 mmol) was added portionwise over 10 min and the reaction mixture was stirred at 0° C. for 30 min. The reaction was quenched with saturated aqueous NH$_4$Cl solution (30 mL) and diluted with EtOAc (100 mL). The layers were separated and the aqueous layer was extracted with ethyl acetate (2×50 mL). Then the combined organic layers were washed with brine (50 mL), dried over Na$_2$SO$_4$, and concentrated under reduced pressure to obtain allylic alcohol (3.5 g crude) as a colorless oil. The obtained crude compound was dissolved in CH$_2$Cl$_2$ (60 mL) and cooled at 0° C.; then imidazole (2.67 g, 39.32 mmol) was added followed by addition of DMAP (0.240 g, 1.96 mmol). Then TBSCl (2.12 g, 19.66 mmol) was added portionwise at same temperature. After stirring the reaction mixture for 12 h, the reaction mixture was diluted with water (40 mL), extracted with $CH_2Cl_2$ (30 mL). The collective organic layer was washed with brine (35 mL) and concentrated. The crude product was purified by column chromatography (silica gel) to yield TBS diene (22), 3.6 g (63% over two steps) as colorless oil.

Data for TBS diene (22): colorless oil; $IR_{vmax}$ (film): 2930, 2856, 1660, 1289 $cm^{-1}$; $^1H$ NMR (500 MHz, $CDCl_3$) δ 5.94 (s, 1H), 5.68 (s, 1H), 5.30 (s, 1H), 4.35 (s, 1H), 2.18-2.09 (m, 2H), 1.80-1.42 (m, 4H), 1.26-1.14 (m, 1H), 0.91 (d, J=6.0 Hz, 15H), 0.09-0.08 (m, 6H); $^{13}C$ NMR (125 MHz, $CDCl_3$) δ 142.7, 128.7, 127.7, 127.6, 69.0, 38.1, 37.4, 35.8, 33.6, 26.1 (3C), 23.4, 18.4, 17.2, 15.5, −4.2, −4.3; HRMS (ESI) calc. for $C_{18}H_{33}OSi$ $[M+H]^+$ 293.1931, found 293.1928.

Example 14

Synthesis of (4aS,5R)-7-((tert-butyldimethylsilyl) oxy)-4a,5-dimethyl-1,2,3,4,4a,5,6,7-octahydronaphthalen-2-ol (23)

To a stirred solution of compound 22 (4.0 g, 13.69 mmol) in $CH_2Cl_2$ (120 mL) at 0° C. was added m-CPBA (~65%), (3.62 g, 13.69 mmol) and stirred the reaction mixture for 30 min at 0° C. Then saturated $NaHCO_3$ solution (40 mL) was added to reaction mixture and stirred for 10 min. Organic layer was separated and aqueous layer was extracted with $CH_2Cl_2$ (40 mL). The combined organic layer was dried over sodium sulfate and concentrated to give crude epoxide as a pale yellow oil. To the crude epoxide (4.0 g, 12.987 mmol) in THF (60 mL) at 0° C. was added LAH (1.2 g, 32.47 mmol) and stirred the reaction mixture at 0° C. for 1 h. The reaction mixture was quenched with saturated $Na_2SO_4$ solution (10 mL) slowly over 5 min. The mixture was diluted with EtOAc (100 mL) and filtered through celite. The organic layer was washed with brine (30 mL), dried over sodium sulfate and evaporated to give crude alcohol (2.1 g) as colorless oil which was carried forward without characterization.

Example 15

Synthesis of (4aS,5R)-4a,5-dimethyl-4,4a,5,6-tetrahydronaphthalen-2(3H)-one (24)

To the above crude alcohol (1.9 g, 6.129 mmol) in $CH_2Cl_2$ (60 mL) at 0° C. was added solid $NaHCO_3$ (0.5 g) followed by DMP (3.9 g, 9.19 mmol) at 0° C. and the reaction mixture was allowed to warm to room temperature over 1 h and stirred for additional 1 h. The reaction mixture was quenched by adding saturated $NaHCO_3$ solution (25 mL). The organic layer was separated, washed with brine (30 mL) and evaporated. The crude product was purified by column chromatography (silica gel) to afford ketone, (1.8 g, 50% over three steps) as a sticky colorless oil. To compound TBS ketone (1.9 g, 6.129 mmol) in $CH_2Cl_2$ (50 mL) was added catalytic $PTSA.H_2O$ (0.040 g) at 30° C. and refluxed the reaction mixture for 1 h. After 1 h, solid $NaHCO_3$ was added to the reaction mixture and solvent was evaporated. The crude compound was purified by column chromatography (silica gel) to afford (−)-dienone (24, 0.550 g, 51%) as a pale yellow oil.

Data for (−)-dienone (24): pale yellow oil; $[α]_D^{19}$=−349.1 (c=0.93, $CHCl_3$) $IR_{vmax}$ (film): 2963, 1646, 1615, 1203 $cm^{-1}$; $^1H$ NMR (400 MHz, $CDCl_3$) δ 6.21-6.17 (m, 1H), 6.10 (d, J=9.7 Hz, 1H), 5.65 (s, 1H), 2.54-2.49 (m, 1H), 2.40 (dd, J=17.2, 3.7 Hz, 1H), 2.19 (dd, J=14.3, 5.2 Hz, 1H), 2.03-1.98 (m, 2H), 1.73-1.66 (m, 2H), 1.00 (s, 3H), 0.92 (d, J=6.8 Hz, 3H); $^{13}C$ NMR (100 MHz, $CDCl_3$) δ 199.8, 163.7, 138.3, 128.2, 123.6, 38.1, 36.2, 34.1, 33.9, 32.5, 15.0, 14.4; HRMS (ESI) calc. for $C_{12}H_{17}O$ $[M+H]^+$ 177.1274, found 177.1272.

Example 16

Synthesis of (4R,4aS)-7,8-dihydroxy-4,4a-dimethyl-4,4a,5,6,7,8-hexahydronaphthalen-2(3H)-one (27)

To a stirred solution of enone (21, 100 mg, 0.57 mmol) in t-BuOH (4 mL) was added $OsO_4$ (0.2 mL, 2.5 M solution in t-BuOH) followed by addition of NMO (199 mg, 1.70 mmol) at 0° C. and stirred the reaction mixture for 2 h. After 2 h the reaction was quenched with saturated $Na_2SO_3$ solution (10 mL) and diluted with EtOAc (20 mL). Organic layer was separated and washed with brine (10 mL), dried over sodium sulfate and evaporated. The crude compound was purified by column chromatography (silica gel) to give diol as a sticky oil (27, 47 mg, 40% yield).

$^1H$ NMR (400 MHz, $CDCl_3$) δ 5.81 (s, 1H), 4.19-4.00 (m, 1H), 3.90-3.67 (m, 1H), 2.96-2.78 (m, 2H), 2.39-2.18 (m, 4H), 1.97-1.83 (m, 1H), 1.27 (s, 3H), 0.97 (d, J=7.3 Hz, 3H); $^{13}C$ NMR (100 MHz, $CDCl_3$) δ 199.9, 169.3, 125.7, 71.2, 69.3, 41.7, 41.6, 40.7, 37.8, 35.8, 18.6, 15.1.

Example 17

Synthesis of (4R,4aS)-6,7-dihydroxy-4,4a-dimethyl-4,4a,5,6,7,8-hexahydronaphthalen-2(3H)-one (28)

To a stirred solution of enone (21, 100 mg, 0.57 mmol) in t-BuOH (4 mL) was added $OsO_4$ (0.2 mL, 2.5 M solution in t-BuOH) followed by addition of NMO (199 mg, 1.70 mmol) at 0° C. and stirred the reaction mixture for 2 h. After 2 h the reaction was quenched with saturated $Na_2SO_3$ solution (10 mL) and diluted with EtOAc (20 mL). Organic layer was separated and washed with brine (10 mL), dried over sodium sulfate and evaporated. The crude compound was purified by column chromatography (silica gel) to give diol 69 mg as a sticky oil (28, 69 mg, 58% yield).

$^1H$ NMR (400 MHz, $CD_3OD$) δ 5.79 (s, 1H), 4.08-4.01 (m, 1H), 4.01-3.92 (m, 1H), 2.82-2.71 (m, 1H), 2.50 (dd, J=3.7, 15.9 Hz, 1H), 2.39-2.28 (m, 1H), 2.22-2.15 (m, 1H), 2.14-2.02 (m, 1H), 1.88 (dd, J=4.6, 12.5 Hz, 1H), 1.70-1.57 (m, 1H), 1.15 (s, 3H), 1.02 (d, J=6.7 Hz, 3H); $^{13}C$ NMR (100 MHz, $CD_3OD$) δ 201.9, 171.1, 127.8, 71.1, 69.2, 49.8, 49.6, 49.4, 48.9, 48.7, 48.5, 42.4, 41.6, 41.0, 40.9, 40.0, 17.4, 15.3.

Example 18

Synthesis of (8R,8aS)-8,8a-dimethyl-1,7,8,8a-tetrahydronaphthalene-2,6-dione (29)

A stirred solution of compound 21 (35 mg, 0.199 mmol in acetonitrile (4 mL) at 0° C. was purged with oxygen gas for 10 min then DBU (30 uL, 0.199 mmol) and reaction mixture was heated at 80° C. for 4 hours. The reaction mixture was diluted with EtOAc (10 mL) and washed with 1N HCl (5 mL) followed by brine (5 mL). The combined organic layer was dried over sodium sulfate and evaporated. Purification by column chromatography (silica gel) gave compound 29 as sticky solid 19 mg (50%)

$^1$H NMR (400 MHz, CDCl$_3$) d=7.07 (d, J=9.8 Hz, 1H), 6.22 (d, J=10.4 Hz, 1H), 6.10 (s, 1H), 2.71 (d, J=15.9 Hz, 1H), 2.51-2.21 (m, 4H), 1.17 (s, 3H), 1.03 (d, J=6.1 Hz, 3H); $^{13}$C NMR (100 MHz, CDCl$_3$) d=198.7, 197.9, 158.8, 143.7, 131.7, 129.7, 49.0, 41.7, 39.8, 39.0, 18.4, 14.6

Example 19

(1S,8aS)-1,8a-dimethyl-1,7,8,8a-tetrahydronaphtha-lene-2,6-dione (30)

Compound 30 was synthesized from compound 29 by following the similar procedure used for the synthesis of compound 29. The data for this compound was matching with the literature report $^1$H NMR (400 MHz, CDCl$_3$) δ 7.19 (d, J=10.0 Hz, 1H), 7.11 (d, J=10.0 Hz, 1H), 6.41 (s, 1H), 6.37 (dd, J=10.1, 1.8 Hz, 1H), 6.27 (d, J=10.0 Hz, 1H), 2.60 (q, J=6.8 Hz, 1H), 1.32 (d, J=6.8 Hz, 3H), 1.23 (s, 3H); $^{13}$C NMR (100 MHz, CDCl$_3$) δ 198.5, 185.3, 157.7, 153.5, 142.6, 131.4, 129.1, 128.7, 49.7, 44.4, 22.4, 7.9.

Example 20

Biological Assay (Cell Adhesion Inhibition Using RBCs)

Flow adhesion assay were performed with commercial microfluidic-well plate and microfluidic flow adhesion system, Bio flux 200. Microfluidic channels were coated by perfusion (1 dyne/cm$^2$, 5 min) and incubated (37° C., 1 h) with 100 ng/ml Fibronectin. Channels were then perfused with complete media to remove unbound Fibronectin. Then a uniform monolayer of HUVEC cells was formed by profusing micro channels with the cell suspension at a pressure of 3 dyne/cm$^2$ for 5 sec and kept for 12 hours incubation to form monolayer. The HUVEC monolayer was activated 25 ng/ml of TNF-α and incubated (37° C., 4 h). Meanwhile RBCs were treated with test compound at 100 μM concentration and incubated in hypoxic condition (3% nitrogen, 5% CO$_2$, 2 h). Flow condition for adhesion assay was pulsatile (1.67 Hz) flow (0.3 dyne/cm$^2$). For adhesion inhibition assay RBCs were diluted (2:50) in PBS. RBCs were perfused over HUVEC monolayer and incubated for 1 h. Unbound cells in micro channels were removed by perfusing complete media. Adherent cells were enumerated. Table 2 depicts percentage of inhibition.

TABLE 2

| Compound | Structure | Inhibition |
|---|---|---|
| 21 | 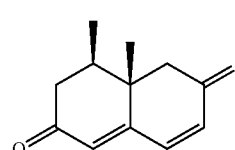 | 78% |
| 28 | 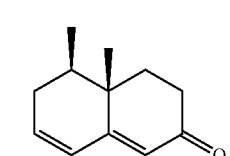 | 56% |
| 29 | 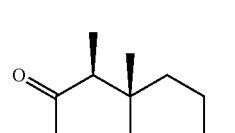 | 70% |
| 24 | 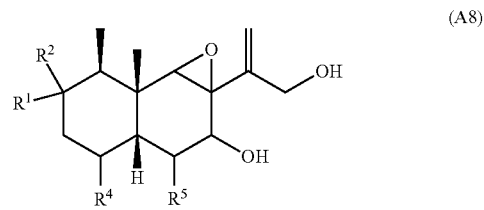 | 67% |
| 30 | 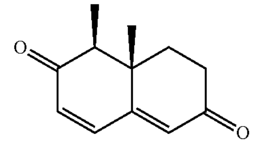 | 72% |

Advantages of the embodiments herein:

Compounds are cell adhesion inhibitors, in particular sickled blood cells

Compounds have potential for treating sickle cell anemia and other blood related disorders The developed route can be scalable and useful for synthesis of diverse analogs.

The invention claimed is:

1. A process for preparing a decalin derivative compound of formula (A8):

(A8)

where:

R$^1$, R$^2$, R$^4$, and R$^5$, are independently chosen from:

hydrogen; or unsubstituted C$_1$-C$_{10}$ alkyl or substituted C$_1$-C$_{10}$ alkyl; or unsubstituted C$_2$-C$_{10}$ alkenyl or C$_2$-C$_{10}$ alkenyl substituted with hydroxy, alkoxy, ester, or —OTBS; or amino, halo, hydroxyl, carbonyl, thiocarbonyl, carboxylate, alkoxy, carbamide, carbamate, or hydrazine, the process comprising:
(a) protecting and following allylic oxidation of a compound according to formula (A5):

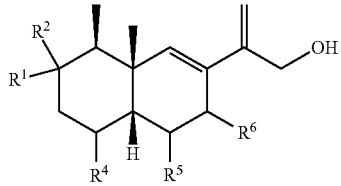

(A5)

where $R^6$ is hydrogen, to afford a compound according to formula (A6):

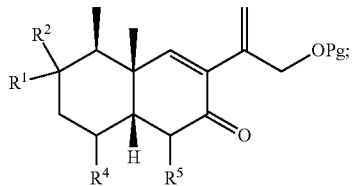

(A6)

(b) epoxidating and deprotecting the compound according to formula (A6) to afford a compound according to formula (A7):

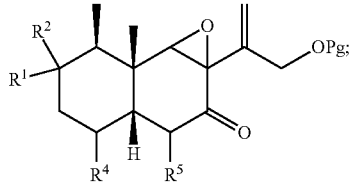

(A7)

and
(c) reducing the compound according to formula (A7) to afford the compound according to formula (A8), wherein:
$R^1$, $R^2$, $R^4$, and $R^5$ in formulas (A5), (A6), (A7) are as defined in the compound of formula (A8); and
Pg in the compounds of formulas (A6) and (A7) is a protecting group.

2. A process for the preparation of a decalin derivative compound of formula (A13):

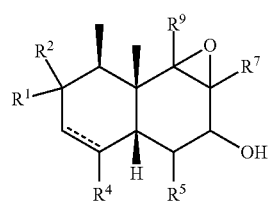

(A13)

where:
$R^1$, $R^2$, $R^4$, $R^5$, $R^7$, and $R^9$ are independently chosen from:
hydrogen; or
unsubstituted C1-$C_{10}$ alkyl or substituted $C_1$-$C_{10}$ alkyl; or
unsubstituted $C_2$-$C_{10}$ alkenyl or $C_2$-$C_{10}$ alkenyl substituted with hydroxy, alkoxy, ester, or —OTBS; or
amino, halo, hydroxyl, carbonyl, thiocarbonyl, carboxylate, alkoxy, carbamide, carbamate, or hydrazine,
or wherein $R^1$, $R^2$, $R^4$, $R^5$, $R^7$, and $R^9$ may be joined to form an unsubstituted or substituted fused cyclic ring, and ▬▬▬ represents a single or double bond, the process comprising:
(a) halogenating a compound according to formula (A9):

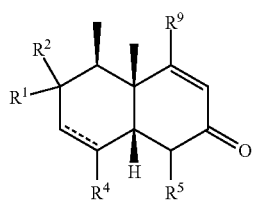

(A9)

to afford a compound according to formula (A10):

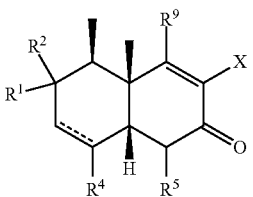

(A10)

where X is a halogen;
(b) performing Suzuki Coupling on the compound according to formula (A10) in the presence of a compound according to formula (X):

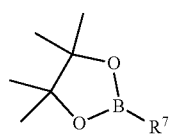

(X)

to afford a compound according to formula (A11):

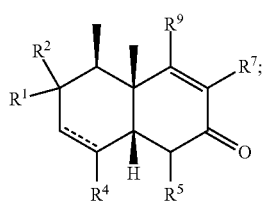

(A11)

(c) forming an epoxide on the compound according to formula (A11) to afford a compound according to formula (Al2):

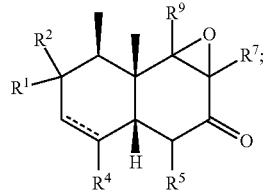

(A12)

and (d) reducing the compound according to formula (Al2) to afford the compound according to formula (A13), wherein:

$R^1, R^2, R^4, R^5, R^7$, and $R^9$ in of formulas (A9), (A10), (X), (A11), (Al2) are as defined in formula (A13).

3. A process for preparing a decalin derivative compound of formula (A21):

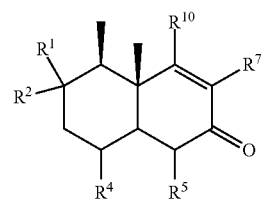

(A21)

where:

$R^1$, $R^2$, $R^4$, $R^5$, $R^7$, and $R^{10}$ are independently chosen from:

hydrogen; or unsubstituted $C_1$-$C_{10}$ alkyl or substituted $C_1$-$C_{10}$ alkyl; or unsubstituted $C_2$-$C_{10}$ alkenyl or $C_2$-$C_{10}$ alkenyl substituted with hydroxy, alkoxy, ester, or —OTBS; or amino, halo, hydroxyl, carbonyl, thiocarbonyl, carboxylate, alkoxy, carbamide, carbamate, or hydrazine, and wherein any of $R^1$, $R^2$, $R^4$, $R^5$, $R^7$, or $R^{10}$ may be joined to form an unsubstituted or substituted fused cyclic ring, the process comprising:

(a) undergoing ozonolysis on a compound according to formula (A14):

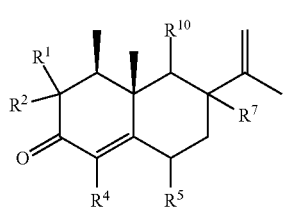

(A14)

to afford a compound according to formula (A15):

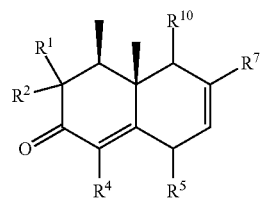

(A15)

(b) rearranging the compound according to formula (A15) to afford a compound according to formula (A16):

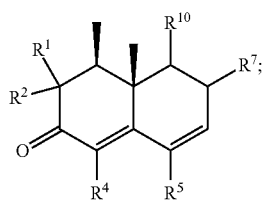

(A16)

(c) reducing and protecting the compound according to formula (A16) to afford a compound according to formula (A17):

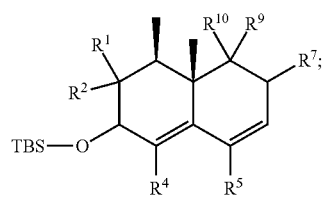

(A17)

where $R^9$ is independently chosen from:

hydrogen; or unsubstituted $C_1$-$C_{10}$ alkyl or substituted $C_1$-$C_{10}$ alkyl; or unsubstituted $C_2$-$C_{10}$ alkenyl or $C_2$-$C_{10}$ alkenyl substituted with hydroxy, alkoxy, ester, or —OTBS, or amino, halo, hydroxyl, carbonyl, thiocarbonyl, carboxylate, alkoxy, carbamide, carbamate, or hydrazine;

(d) epoxidating and reducing the compound according to formula (A17) to afford a compound according to formula (A18):

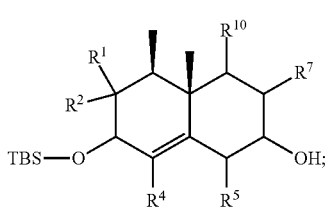

(A18)

(e) oxidating, deprotecting, and rearranging the compound according to formula (A18), to afford a compound according to formula (A19):

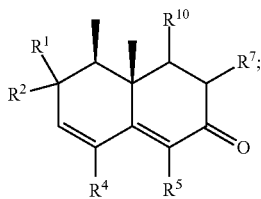
(A19)

hydrogenating the compound according to formula (A19) to afford a compound according to formula (A20):

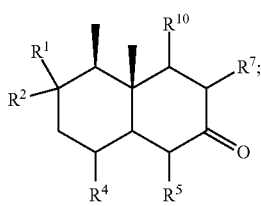
(A20)

and (g) oxidating the compound according to formula (A20) to afford the compound according to formula (A21), wherein:
$R^1$, $R^2$, $R^4$, $R^5$, $R^7$, and $R^{10}$ in the compounds of formulas (A14), (A15), (A16), (A17), (A18), (A19), and (A20), are as defined in the compound of formula (A21); and
TBS in formulas (A17) and (A18) is tert-butyldimethylsilyl.

4. A process for preparing a decalin derivative compound of formula (A23) or formula (A25):

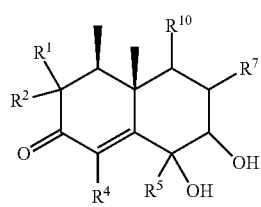
(A25)

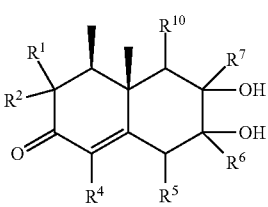
(A23)

where:
R', $R^2$, $R^4$, $R^5$, $R^7$, and $R^{10}$ are independently chosen from:
hydrogen; or
unsubstituted $C_1$-$C_{10}$ alkyl or substituted $C_1$-$C_{10}$ alkyl; or
unsubstituted $C_2$-$C_{10}$ alkenyl or $C_2$-$C_{10}$ alkenyl substituted with hydroxy, alkoxy, ester, or —OTBS; or
amino, halo, hydroxyl, carbonyl, thiocarbonyl, carboxylate, alkoxy, carbamide, carbamate, or hydrazine,
wherein any of $R^1$, $R^2$, $R^4$, $R^5$, $R^7$, and $R^{10}$ may be joined to form an unsubstituted or substituted fused cyclic ring,
the process comprising:
dihydroxylating a compound according to formula (A22):

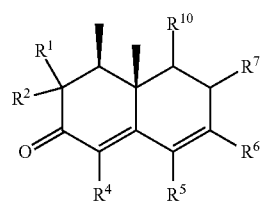
(A22)

wherein $R^6$ is hydrogen and wherein $R_1$, $R_2$, $R_4$, $R_5$, $R^7$, and $R^{10}$ in formula (A22) are as defined in the compound according to formula (A23) to afford the compound according to formula (A23); or
dihydroxylating a compound according to formula (A24):

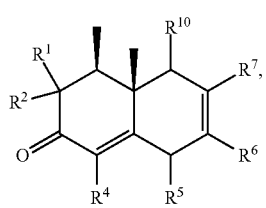
(A24)

wherein $R^6$ is hydrogen and wherein $R_1$, $R_2$, $R_4$, $R_5$, $R^7$, and $R^{10}$ in formula (A24) are as defined in the compound according to formula (A25) to afford the compound according to formula (A25).

5. A method for treating sickle cell anemia, the method comprising:
administering a therapeutically effective amount of a decalin derivative compound prepared according to the process of claim 1.

6. A method for treating sickle cell anemia, the method comprising:
administering a therapeutically effective amount of a decalin derivative compound prepared according to the process of claim 2.

7. A method for treating sickle cell anemia, the method comprising:
administering a therapeutically effective amount of a decalin derivative compound prepared according to the process of claim 4.

* * * * *